United States Patent
Tabata

(10) Patent No.: US 12,396,629 B2
(45) Date of Patent: Aug. 26, 2025

(54) ENDOSCOPE LIGHT SOURCE DEVICE AND LIGHT QUANTITY ADJUSTING METHOD

(71) Applicant: OLYMPUS CORPORATION, Tokyo (JP)

(72) Inventor: Motoki Tabata, Akishima (JP)

(73) Assignee: OLYMPUS CORPORATION, Tokyo (JP)

( * ) Notice: Subject to any disclaimer, the term of this patent is extended or adjusted under 35 U.S.C. 154(b) by 363 days.

(21) Appl. No.: 17/885,057

(22) Filed: Aug. 10, 2022

(65) Prior Publication Data

US 2022/0378284 A1 Dec. 1, 2022

Related U.S. Application Data

(63) Continuation of application No. PCT/JP2020/006373, filed on Feb. 18, 2020.

(51) Int. Cl.
*A61B 1/06* (2006.01)
*A61B 1/00* (2006.01)
*A61B 1/07* (2006.01)

(52) U.S. Cl.
CPC ........ *A61B 1/0655* (2022.02); *A61B 1/00097* (2022.02); *A61B 1/0638* (2013.01); *A61B 1/0669* (2013.01); *A61B 1/07* (2013.01)

(58) Field of Classification Search
CPC .............. A61B 1/00097; A61B 1/0655; A61B 1/0638; A61B 1/0661; A61B 1/0669; A61B 1/0684; A61B 1/07; A61B 1/00096; A61B 1/00117; A61B 1/00126; A61B 1/00165; A61B 1/00186; A61B 1/043; A61B 1/045

See application file for complete search history.

(56) References Cited

U.S. PATENT DOCUMENTS

| 8,803,056 B2 | 8/2014 | Shirota et al. |
| 11,583,173 B2 * | 2/2023 | Ito .................. A61B 1/0669 |
| 2011/0208004 A1 | 8/2011 | Feingold et al. |

(Continued)

FOREIGN PATENT DOCUMENTS

| CN | 103619234 A | 3/2014 |
| JP | 2011165607 A * | 8/2011 |

(Continued)

OTHER PUBLICATIONS

International Search Report dated May 26, 2020 issued in PCT/JP2020/006373.

*Primary Examiner* — Ryan N Henderson
(74) *Attorney, Agent, or Firm* — Scully, Scott, Murphy & Presser, P.C.

(57) ABSTRACT

An endoscope light source device includes: a box that is connectable to a light guide of an endoscope; a first light source configured to emit light of a first wavelength band; a second light source configured to emit light of a second wavelength band; a multiplexer configured to multiplex the light emitted by the first light source and the light emitted by the second light source; a diffuser configured to diffuse part of the light multiplexed by the multiplexer to an outside of an optical path for input to the light guide; a light quantity sensor configured to detect quantity of at least part of the light diffused by the diffuser; and an illumination controller configured to control quantity of light to be emitted from at least one of the first light source and the second light source.

15 Claims, 10 Drawing Sheets

(56) References Cited

U.S. PATENT DOCUMENTS

| | | | |
|---|---|---|---|
| 2013/0345517 A1* | 12/2013 | Morimoto | A61B 1/0661 600/178 |
| 2014/0054450 A1* | 2/2014 | Shirota | G02B 23/26 250/226 |
| 2015/0099932 A1* | 4/2015 | Morimoto | H05B 45/12 315/153 |
| 2017/0105258 A1* | 4/2017 | Sakai | A61B 1/0661 |
| 2017/0202445 A1* | 7/2017 | Sakai | G02B 23/2469 |
| 2017/0231502 A1* | 8/2017 | Nagaoka | A61B 1/0684 600/476 |
| 2018/0368671 A1* | 12/2018 | Nakayama | A61B 1/0676 |
| 2019/0068864 A1* | 2/2019 | Ohashi | A61B 1/044 |
| 2020/0029786 A1* | 1/2020 | Morimoto | A61B 1/00006 |
| 2020/0234439 A1* | 7/2020 | Chang | G06T 7/0012 |
| 2021/0085186 A1* | 3/2021 | Yamakawa | A61B 1/00 |
| 2023/0420631 A1* | 12/2023 | Kuboi | A61B 1/0669 |
| 2024/0000303 A1* | 1/2024 | Ito | A61B 1/0655 |

FOREIGN PATENT DOCUMENTS

| | | |
|---|---|---|
| JP | 5909091 B2 | 4/2016 |
| WO | 2010059197 A2 | 5/2010 |
| WO | 2010100898 A1 | 9/2010 |
| WO | 2013150897 A1 | 10/2013 |
| WO | 2018003241 A1 | 1/2018 |

* cited by examiner

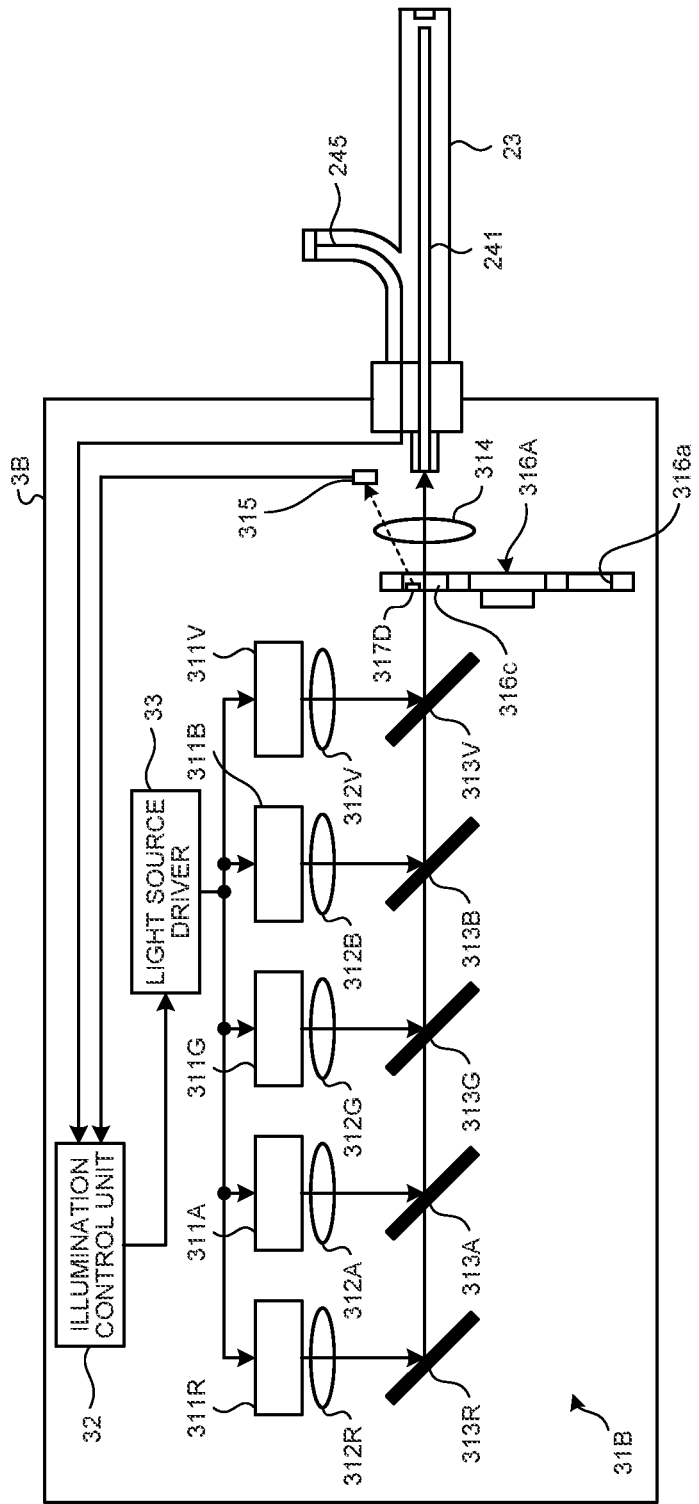

ENDOSCOPE LIGHT SOURCE DEVICE AND LIGHT QUANTITY ADJUSTING METHOD

CROSS-REFERENCE TO RELATED APPLICATION

This application is a continuation of International Application No. PCT/JP2020/006373, filed on Feb. 18, 2020, the entire contents of which are incorporated herein by reference.

BACKGROUND

1. Technical Field

The present disclosure relates to an endoscope light source device and a light quantity adjusting method.

2. Related Art

Endoscope systems for observation of the interiors of subjects have been used in the medical field. Typically, an elongated flexible insertion portion of an endoscope is inserted into a subject, such as a patient, and the interior of the subject is illuminated with illumination light from a distal end of this insertion portion. A light source device that supplies the illumination light is connected to the endoscope.

In an endoscope system, quantity of illumination light is controlled for stable irradiation with illumination light, against change in quantity of illumination light due to temporal change that occurs in a light source or an optical member in a light source device. In a known technique for detection of quantity of illumination light emitted from a light source device, part of the illumination light is input to an optical fiber and the input light is detected by a sensor (see, for example, Japanese Patent No. 5909091). Furthermore, in another known technique, part of light is reflected immediately before the light is emitted from a light source device and the light that has deviated from the optical path by the reflection is detected (for example, see Japanese Patent Application Laid-open No. 2011-165607 and International Publication WO No. 2010/100898).

SUMMARY

In some embodiments, an endoscope light source device includes: a box that is connectable to a light guide of an endoscope; a first light source that is arranged in the box, the first light source being configured to emit light of a first wavelength band; a second light source that is arranged in the box, the second light source being configured to emit light of a second wavelength band different from the first wavelength band; a multiplexer configured to multiplex the light emitted by the first light source and the light emitted by the second light source; a diffuser that is provided between the multiplexer and an input end of the light guide connected to the box, the diffuser being configured to diffuse part of the light multiplexed by the multiplexer to an outside of an optical path for input to the light guide; a light quantity sensor that is provided outside the optical path for the input to the light guide, the light quantity sensor being configured to detect quantity of at least part of the light diffused by the diffuser; and an illumination controller configured to control, based on a result detected by the light quantity sensor, quantity of light to be emitted from at least one of the first light source and the second light source.

In some embodiments, an endoscope light source device includes: a light guide configured to guide light input to an input end of the light guide to a distal end of an insertion portion; a first light source configured to emit light of a first wavelength band; a second light source configured to emit light of a second wavelength band different from the first wavelength band; a multiplexer configured to multiplex the light emitted by the first light source and the light emitted by the second light source; a diffuser that is provided between the multiplexer and the input end of the light guide, the diffuser being configured to diffuse part of the light multiplexed by the multiplexer to an outside of an optical path for input to the light guide; a light quantity sensor that is provided outside the optical path for the input to the light guide, the light quantity sensor being configured to detect quantity of at least part of the light diffused by the diffuser; and an illumination controller configured to control, based on a result detected by the light quantity sensor, quantity of light to be emitted by at least one of the first light source and the second light source.

In some embodiments, a light quantity adjusting method includes: emitting light of a first wavelength band by a first light source; emitting light of a second wavelength band by a second light source; multiplexing, by a multiplexer, the light emitted by the first light source and the light emitted by the second light source, for input to a light guide provided in an endoscope; providing a diffuser between the multiplexer and an input end of the light guide; diffusing, by the diffuser, part of the light multiplexed by the multiplexer to an outside of an optical path for the input to the light guide; providing a light quantity sensor outside the optical path for the input to the light guide; detecting, by the light quantity sensor, quantity of at least part of the light diffused by the diffuser; and controlling, by an illumination controller, quantity of light emitted by at least one of the first light source and the second light source based on a result detected by the light quantity sensor.

The above and other features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 14 is a diagram illustrating a configuration of a light source device in an endoscope system according to a sixth embodiment of the disclosure.

DETAILED DESCRIPTION

Modes for implementing the disclosure (hereinafter, referred to as "embodiments") will be described hereinafter. A medical endoscope system described with respect to the embodiments is for capturing and displaying images of the interiors of subjects, such as patients, and is an example of a system according to the disclosure, the system including an endoscope light source device. The disclosure is not limited by these embodiments. Description will be made by assignment of the same reference sign to portions that are the same, throughout the drawings.

First Embodiment

Figure 1:
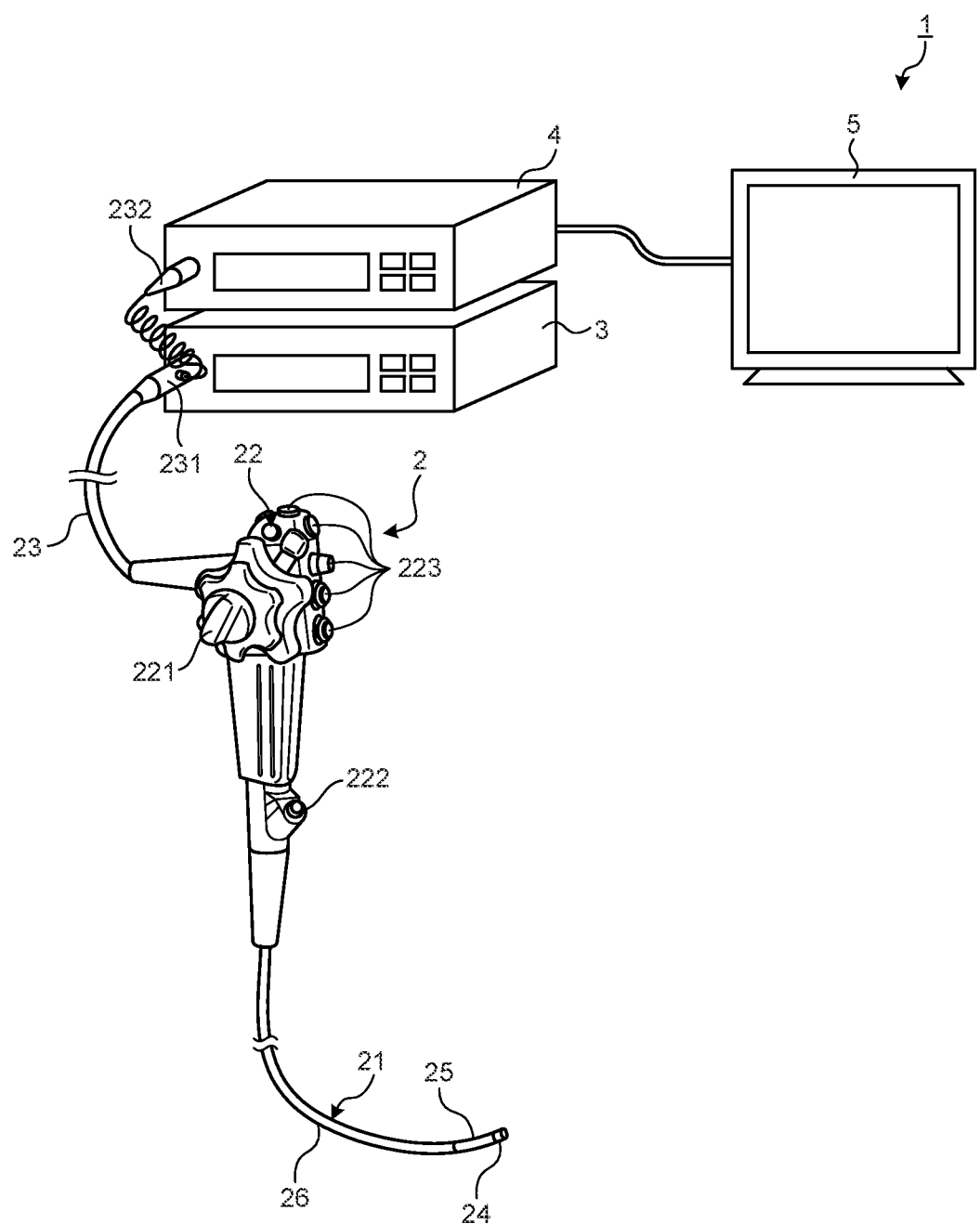
FIG. 1 is a diagram illustrating a schematic configuration of an endoscope system according to a first embodiment of the disclosure.
Figure 2:
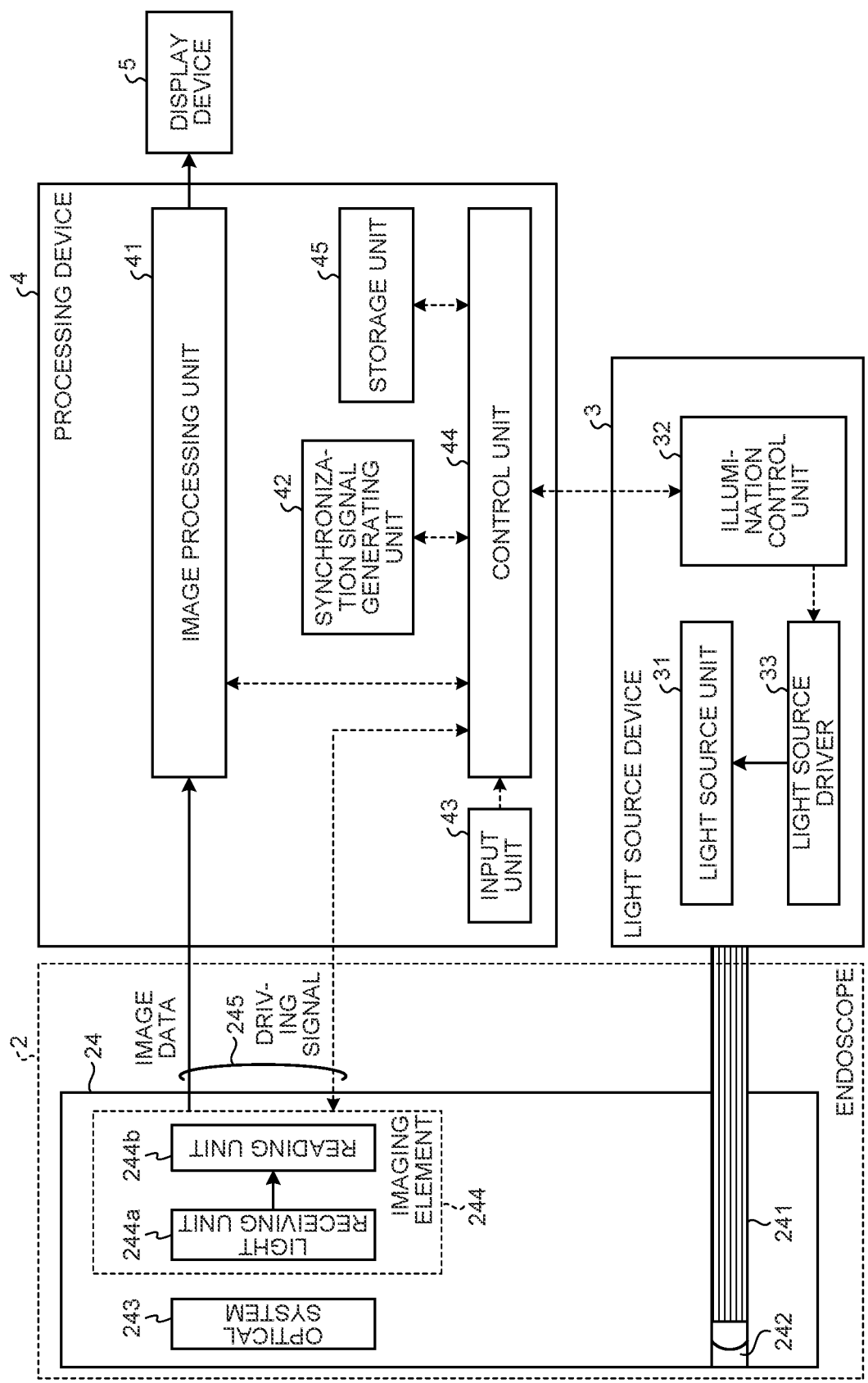
FIG. 2 is a block diagram illustrating a schematic configuration of the endoscope system according to the first embodiment of the disclosure.

FIG. 1 is a diagram illustrating a schematic configuration of an endoscope system according to a first embodiment of the disclosure. FIG. 2 is a block diagram illustrating a schematic configuration of the endoscope system according to the first embodiment.

An endoscope system 1 illustrated in FIG. 1 and FIG. 2 includes: an endoscope 2 for capturing of an in-vivo image of a subject by insertion of a distal end portion of the endoscope 2 into the subject; a light source device 3 that generates illumination light to be output from a distal end of the endoscope 2; a processing device 4 that performs predetermined signal processing on an imaging signal captured by the endoscope 2 and integrally controls overall operation of the endoscope system 1; and a display device 5 that displays the in-vivo image generated through the signal processing by the processing device 4.

The endoscope 2 includes: an insertion portion 21 that has flexibility and is elongated; an operating unit 22 that is connected to a proximal end of the insertion portion 21 and receives input of various operation signals; and a universal cord 23 that extends from the operating unit 22 in a direction different from a direction in which the insertion portion 21 extends, the universal cord 23 having various cables built therein for connection to the light source device 3 and the processing device 4.

The insertion portion 21 includes: a distal end portion 24 having an imaging element 244 built therein, the imaging element 244 having two-dimensionally arrayed pixels that generate a signal by receiving light and photoelectrically converting the light; a bending portion 25 that is formed of plural bending pieces and is bendable; and a flexible tube portion 26 that is connected to a proximal end of the bending portion 25, has flexibility, and is elongated. The insertion portion 21 is inserted into a body cavity of the subject, and captures, by means of the imaging element 244, an image of an object, such as body tissue at a position where external light is unable to reach.

The distal end portion 24 includes: a light guide 241 that is configured by use of, for example, glass fiber and that serves as a light guiding path for light emitted by the light source device 3; an illumination lens 242 that is provided at a distal end of the light guide 241; an optical system 243 for condensing light; and the imaging element 244 (an imaging unit) that is provided at an image forming position of the optical system 243, receives the light condensed by the optical system 243, photoelectrically converts the light into an electric signal, and performs predetermined signal processing on the electric signal.

The optical system 243 is configured by use of one or plural lenses and has: an optical zooming function for change of the angle of view; and a focusing function for change of the focus.

The imaging element 244 generates an electric signal (an image signal) by photoelectrically converting light from the optical system 243. Specifically, the imaging element 244 includes: a light receiving unit 244a having plural pixels, which are arrayed in a matrix, each of which has a photodiode that accumulates electric charge according to quantity of light and a condenser that converts an electric charge transferred from the photodiode into a voltage level, and each of which generates an electric signal by photoelectrically converting light from the optical system 243; and a reading unit 244b that sequentially reads electric signals generated by pixels freely set as targets to be read, from the plural pixels of the light receiving unit 244a, and that outputs the read electric signals as image signals. The imaging element 244 is implemented by use of, for example, a charge coupled device (CCD) image sensor, or a complementary metal oxide semiconductor (CMOS) image sensor.

The endoscope 2 has a memory (not illustrated in the drawings) that stores: an execution program and a control program, for the imaging element 244 to execute various operations; and data including identification information of the endoscope 2. The identification information includes, for example, unique information (ID), the model year, specification information, and the transmission scheme, of the endoscope 2. Furthermore, the memory may temporarily store, for example, image data generated by the imaging element 244.

The operating unit 22 includes: a bending knob 221 that bends the bending portion 25 upward, downward, leftward, and/or rightward; a treatment tool insertion portion 222 through which a treatment tool, such as biopsy forceps, an electric knife, or an examination probe, is inserted into the body cavity of the subject; and plural switches 223 serving as an operation input unit through which peripheral device operating instruction signals are input, the peripheral device operating instruction signals being for, in addition to the processing device 4, a gas feeding means, a water feeding means, and screen display control, for example. The treatment tool inserted from the treatment tool insertion portion 222 comes out from an opening (not illustrated in the drawings) via a treatment tool channel (not illustrated in the drawings) in the distal end portion 24.

The universal cord 23 has, built therein, at least the light guide 241 and a cable assembly 245 that is an assembly of one or plural signal lines. The universal cord 23 is branched at an opposite end portion of the universal cord 23, the opposite end portion being opposite to an end portion connected to the operating unit 22. A connector 231 attachable to and detachable from the light source device 3 and a connector 232 attachable to and detachable from the processing device 4 are provided at the branched end portion of the universal cord 23. A part of the light guide 241 extending comes out from an end portion of the connector 231. The universal cord 23 propagates illumination light emitted from the light source device 3 to the distal end portion 24 via the connector 231 (the light guide 241), the operating unit 22, and the flexible tube portion 26. Furthermore, the universal cord 23 transmits an image signal captured by the imaging element 244 provided in the distal end portion 24 to the processing device 4 via the connector 232. The cable assembly 245 includes a signal line for transmission of imaging signals, a signal line for transmission of driving signals for driving the imaging element 244, and a signal line for transmission and reception of information including the unique information related to the endoscope 2 (the imaging element 244). With respect to the first embodiment, an electric signal is described to be transmitted by use of a signal line, but an optical signal may be transmitted, or a signal may be transmitted between the endoscope 2 and the processing device 4 by wireless communication.

Figure 3:
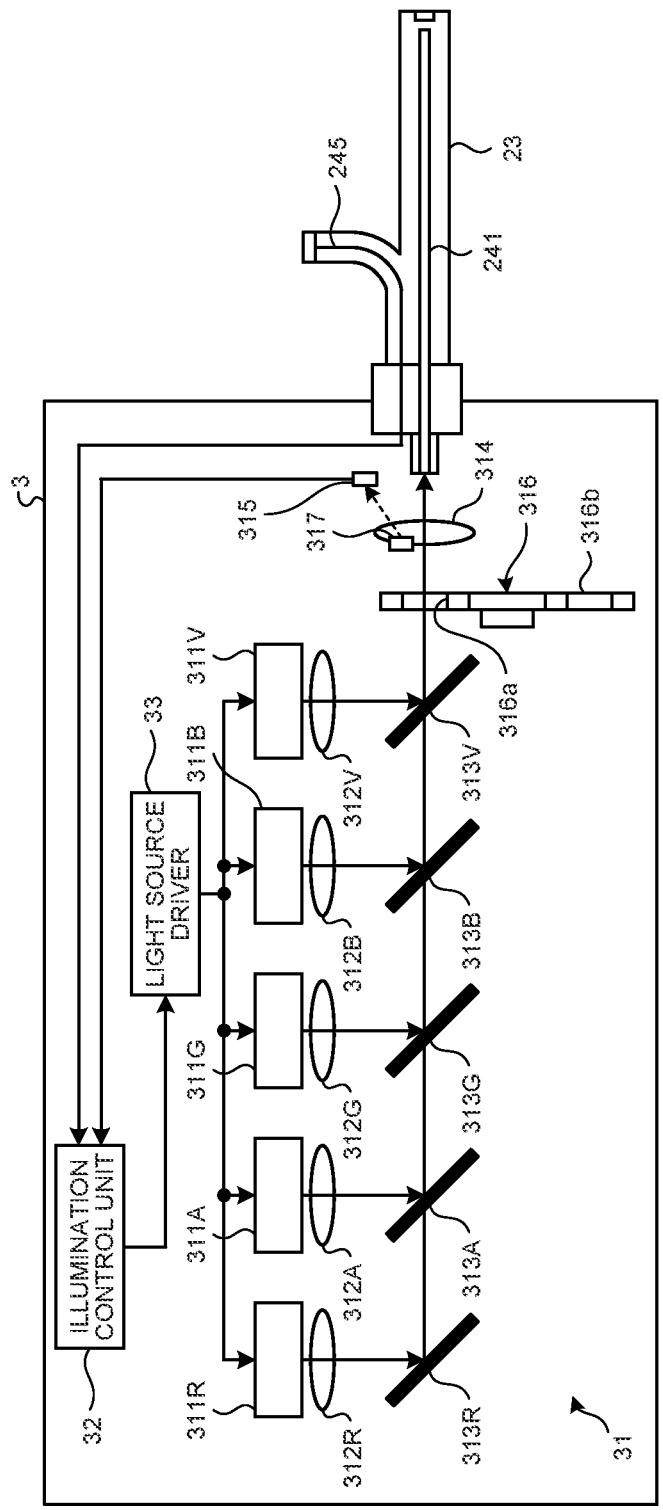
FIG. 3 is a diagram illustrating a configuration of a light source device in the endoscope system according to the first embodiment of the disclosure.

A configuration of the light source device 3 will be described next. The light source device 3 includes a light source unit 31, an illumination control unit 32, and a light source driver 33. FIG. 3 is a diagram illustrating a configuration of a light source device in the endoscope system according to the first embodiment of the disclosure.

The light source unit 31 is configured by use of, for example: plural light sources that emit plural types of illumination light having wavelength bands different from one another; and plural lenses. Driving these light sources causes illumination light to be emitted by the light source unit 31, the illumination light including light of a predetermined wavelength band. Specifically, the light source unit 31 includes: a first light source 311V; a second light source 311B; a third light source 311G; a fourth light source 311A; a fifth light source 311R; a lens 312V that condenses violet light emitted by the first light source 311V; a lens 312B that condenses blue light emitted by the second light source 311B; a lens 312G that condenses green light emitted by the third light source 311G; a lens 312A that condenses amber light emitted by the fourth light source 311A; a lens 312R that condenses red light emitted by the fifth light source 311R; a first dichroic mirror 313V; a second dichroic mirror 313B; a third dichroic mirror 313G; a fourth dichroic mirror 313A; a fifth dichroic mirror 313R; a condenser lens 314 that condenses wavelengths output by the light sources and guides the condensed wavelengths to the light guide 241; a light quantity sensor 315 that detects quantity of part of light that has passed through the condenser lens 314; a rotating filter 316; and a diffuser 317. These light sources are implemented by use of, for example, any of LED light sources and laser light sources.

The first light source 311V emits light (violet light) of a wavelength band of 380 nm to 420 nm.

The second light source 311B emits light (blue light) of a wavelength band of 420 nm to 495 nm.

The third light source 311G emits light (green light) of a wavelength band of 495 nm to 570 nm.

The fourth light source 311A emits light (amber light) of a wavelength band of 590 nm to 620 nm.

The fifth light source 311R emits light (red light) of a wavelength band of 620 nm to 750 nm.

The first light source 311V to the fifth light source 311R are formed of light emitting diode (LEDs), laser diodes (LDs), or a combination of an LED/LEDs and an LD/LDs.

The above mentioned wavelength bands are just examples, and depending on types of the light sources, any light source having a wavelength band partly overlapping a wavelength of light emitted by another one of the light sources may be used.

The dichroic mirrors 313V, 314B, 314G, 314A, and 314R turn light from the light sources, cause the light to travel on the same optical axis, and thereby multiplexes the light. A multiplexer is configured by use of these dichroic mirrors.

The first dichroic mirror 313V turns light of the wavelength band emitted by the first light source 311V and transmits therethrough light of the other wavelength bands.

The second dichroic mirror 313B turns light of the wavelength band emitted by the second light source 311B and transmits therethrough light of the other wavelength bands.

The third dichroic mirror 313G turns light of the wavelength band emitted by the third light source 311G and transmits therethrough light of the other wavelength bands.

The fourth dichroic mirror 313A turns light of the wavelength band emitted by the fourth light source 311A and transmits therethrough light of the other wavelength bands.

The fifth dichroic mirror 313R turns light of the wavelength band emitted by the fifth light source 311R and transmits therethrough light of the other wavelength bands.

This first embodiment may just include at least the second light source 311B, the third light source 311G, and the fifth light source 311R for emission of illumination light having colors, red, blue, and green. The lenses and the dichroic mirrors are provided according to the light sources that are installed.

The rotating filter 316 has a hole 316a where illumination light that has been multiplexed is passed through and a wavelength selecting filter 316b for selection of a wavelength band of light to be input to the light guide 241. The rotating filter 316 is provided between the first dichroic mirror 313V and the condenser lens 314, and inserts or removes the hole 316a or the wavelength selecting filter 316b into or from an optical path for illumination light by rotating itself under control of the illumination control unit 32. In a case where a wavelength band of excitation light to be emitted to the subject is to be guided to the light guide 241 for fluorescent observation, for example, the rotating filter 316 inserts the corresponding wavelength selecting filter into the optical path.

Figure 4:
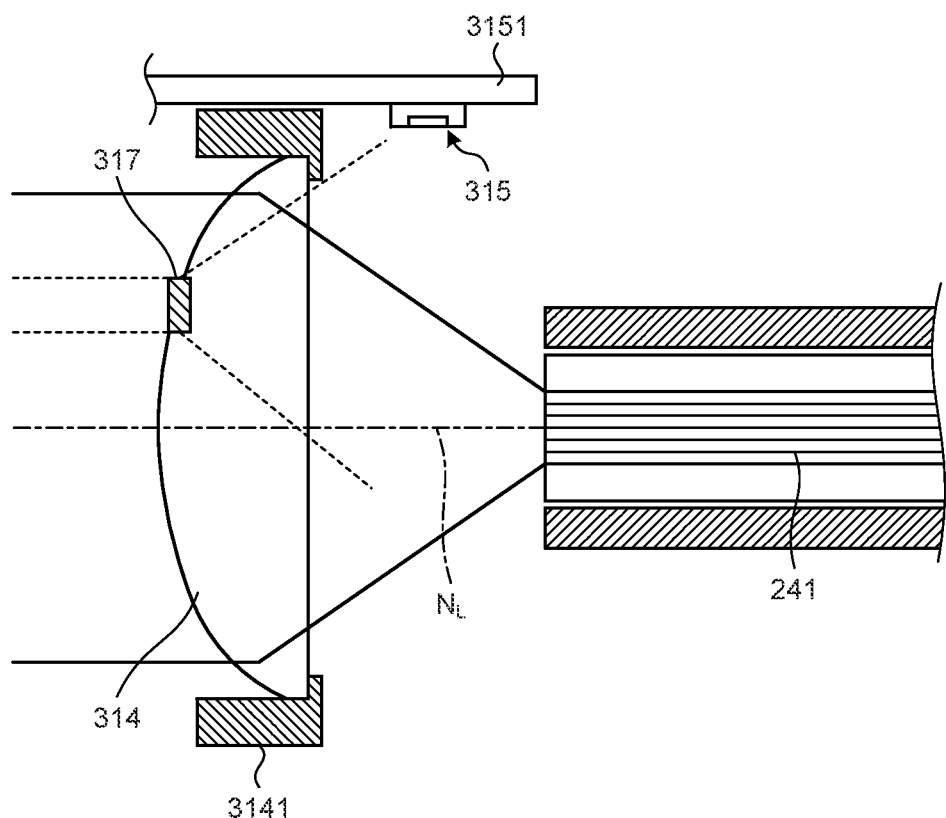
FIG. 4 is a diagram illustrating a configuration of a portion of the light source device, the portion being where a light guide is connected.
Figure 5:
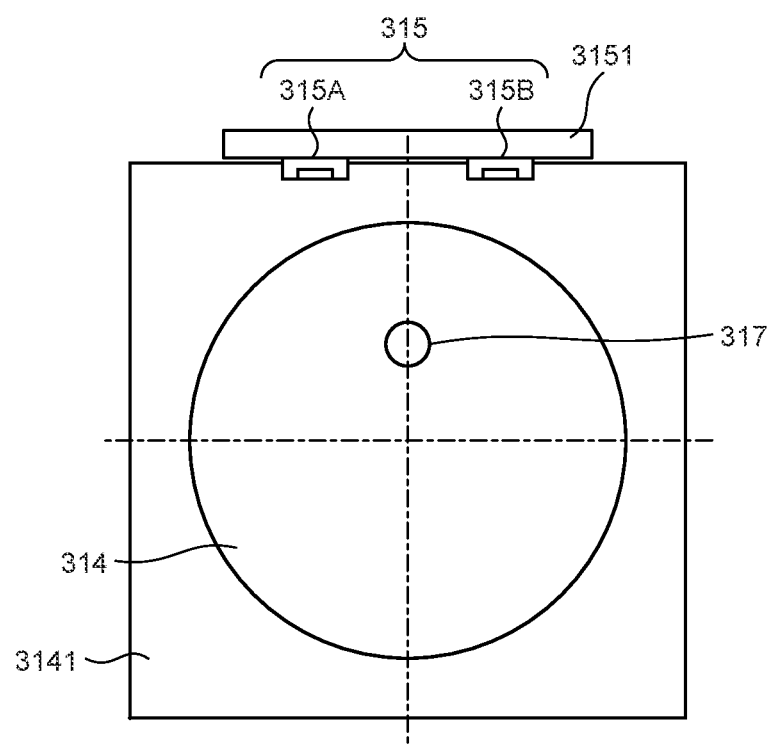
FIG. 5 is a plan view of a region around a condenser lens in the light source device, as viewed along an optical axis direction.

FIG. 4 is a diagram illustrating a configuration of a portion of the light source device, the portion being where a light guide is connected. FIG. 5 is a plan view of a region around a condenser lens in the light source device, as viewed along an optical axis direction. The condenser lens 314 is held by a lens holder 3141 supported on a casing (a box) of the light source device 3.

The light quantity sensor 315 includes a first sensor 315A having sensitivity to light of the wavelength bands respectively emitted by the second light source 311B, the third light source 311G, and the fifth light source 311R, and a second sensor 315B having sensitivity to light of the wavelength bands respectively emitted by the first light source 311V, the third light source 311G, and the fourth light source 311A (see FIG. 5). The first sensor 315A and the second sensor 315B output detected values (light quantity values) for the light of the respective wavelength bands to the illumination control unit 32. The light quantity sensor 315 outputs, as a detected value for light emitted by the third light source 311G, at least one of detected values by the first sensor 315A and the second sensor 315B, to the illumination control unit 32.

The light quantity sensor 315 is provided at a position not overlapping the optical path (an optical axis $N_L$) of illumination light and on one side of the condenser lens 314, the one side being close to the light guide 241 (a downstream side along the optical path), and near the condenser lens 314. The light quantity sensor 315 detects quantity of part of multiplexed light resulting from multiplexing of light emitted from the first light source 311V to the fifth light source 311R. The first sensor 315A and the second sensor 315B are held by a supporting member 3151 supported on the casing of the light source device 3. The first sensor 315A and the second sensor 315B are each configured by use of a sensor including photodiodes having sensitivity to target wavelength bands, a CCD image sensor, or a CMOS image sensor. The CCD image sensor or the CMOS image sensor, which may be used as the light quantity sensor 315, has filters that respectively transmit therethrough light from the light sources and that are arranged upstream of pixels. Using the CCD image sensor or the CMOS image sensor as the light quantity sensor 315 enables detection in detail of change in quantity of emitted light associated with change in light quantity distribution. In contrast, the sensor including the photodiodes having sensitivity to the target wavelength bands enables the light quantity sensor 315 to be formed more inexpensively, as compared to a case where the CCD image sensor or the CMOS sensor is used.

The diffuser 317 is provided in the condenser lens 314 and diffuses light incident thereon. The diffuser 317 is formed by surface processing of the condenser lens 314. The diffuser 317 is provided on a surface of the condenser lens 314, the surface being on one side of the condenser lens 314, the one side being where the multiplexer is provided, and is thus provided between the condenser lens 314 and the multiplexer. The diffuser 317 has a surface roughness higher than that of a surface of the condenser lens 314, the surface excluding a portion where the diffuser 317 is formed.

The diffuser 317 is provided on a side of the condenser lens 314, the side being opposite to a side facing the light guide 241, and at a position deviated from the optical axis $N_L$ of an illumination optical system including the condenser lens 314. The light quantity sensor 315 is provided in a range of output from the condenser lens 314, the output being that of light diffused by the diffuser 317. That is, part of the light diffused by the diffuser 317 is input to the light quantity sensor 315 via the condenser lens 314.

An area over which the diffuser 317 is provided on the condenser lens 314 is preferably 2% or less of an effective diameter area of the condenser lens 314. Fulfilling the above described conditions enables sufficient quantity of illumination light to be guided to the light guide 241 and detected light to be diffused.

The light source driver 33 causes, under control of the illumination control unit 32, the light sources to emit light, by supplying electric current to the light sources.

The light source unit 31 emits illumination light of different colors, blue illumination light through emission of light by the first light source 311V and the second light source 311B, green illumination light through emission of light by the third light source 311G, and red illumination light through emission of light by the fourth light source 311A and the fifth light source 311R.

The red (R) illumination light, the green (G) illumination light, and the blue (B) illumination light may hereinafter be simply referred to as R illumination light, G illumination light, and B illumination light, respectively.

On the basis of a control signal (a light adjusting signal) from an control unit 37, the illumination control unit 32 controls driving timing of the light sources. Furthermore, on the basis of detected values of light of the wavelength bands obtained from the light quantity sensor 315, the illumination control unit 32 performs feedback control of electric energy to be supplied to the light sources. For example, the illumination control unit 32 outputs, to the light sources, output values at which proportions of quantities of light emitted from the light sources become preset proportions. In addition, on the basis of an image generated by an image processing unit 41, the illumination control unit 32 may determine a quantity of green (G) illumination light at which brightness of the image has an adequate value, from a correlation between brightness of a green (G) component and detected values of green (G) illumination light obtained from the light quantity sensor 315. Furthermore, a quantity of light at which brightness of each color component becomes adequate may be determined from a proportion of a detected value of red (R) illumination light and a proportion of a detected value of blue (B) illumination light to a detected value of green (G) illumination light.

A configuration of the processing device 4 will be described next by reference to FIG. 2 again. The processing device 4 includes the image processing unit 41, a synchronization signal generating unit 42, an input unit 43, a control unit 44, and a storage unit 45.

The image processing unit 41 receives, from the endoscope 2, image data for illumination light of each color captured by the imaging element 244. In a case where the image processing unit 41 has received analog image data from the endoscope 2, the image processing unit 41 generates a digital imaging signal by performing A/D conversion. In a case where the image processing unit 41 has received image data as an optical signal, from the endoscope 2, the image processing unit 41 generates digital image data by performing photoelectric conversion.

The image processing unit 41 generates an image by performing predetermined image processing on image data received from the endoscope 2 and outputs the image to the display device 5. This predetermined image processing may include any of synchronization processing, gradation correction processing, and color correction processing. The synchronization processing is processing in which sets of image data of R, G, and B color components are synchronized with one another. The color correction processing is processing in which gradation is corrected for image data. The color correction processing is processing in which color tones are corrected for image data. The image processing unit 41 generates an imaging signal that has been processed, which may hereinafter be simply referred to as an imaging signal, the imaging signal including an in-vivo image generated by the image processing described above. The image processing unit 41 may perform gain adjustment according to brightness of the image. The image processing unit 41 is configured by use of a general-purpose processor, such as a central processing unit (CPU), or a special-purpose processor, such as an arithmetic circuit that executes a specific function, like an application specific integrated circuit (ASIC).

The image processing unit 41 may be configured to have a frame memory that holds R image data, G image data, and B image data.

The synchronization signal generating unit 42 generates a clock signal (a synchronization signal) serving as a basis of operation of the processing device 4 and outputs the generated synchronization signal to the light source device 3, the image processing unit 41, the control unit 44, and the endoscope 2. The synchronization signal generated by the synchronization signal generating unit 42 includes a horizontal synchronization signal and a vertical synchronization signal.

Accordingly, the light source device 3, the image processing unit 41, the control unit 44, and the endoscope 2 operate in synchronization with one another on the basis of the synchronization signal generated.

The input unit 43 is implemented by use of a keyboard and a mouse, switches, and/or a touch panel; and receives input of various signals, such as operation instruction signals for instructing the endoscope system 1 to operate. The input unit 43 may include a switch provided in the operating unit 22, or a portable terminal, such as an external tablet computer.

The control unit 44 performs drive control of elements/units/devices including the imaging element 244 and the light source device 3, and input and output control of information for these elements/units/devices. The control unit 44 refers to control information data (for example, readout timing) for imaging control stored in the storage unit 45 and transmits the control information data as a driving signal to the imaging element 244 via a predetermined signal line included in the cable assembly 245. The control unit 44 is configured by use of: a general-purpose processor, such as a CPU; or a special-purpose processor, such as an arithmetic circuit that executes a specific function, like an ASIC.

The storage unit 45 stores therein various programs for operating the endoscope system 1, and data including various parameters needed for the operation of the endoscope system 1. The storage unit 45 also stores therein identification information of the processing device 4. This identification information includes, for example, unique information (ID), the model year, and specification information, of the processing device 4. Furthermore, the storage unit 45 includes an illumination information storage unit 451 that stores therein information related to, for example, arrangement of the light sources included in the light source device 3. The illumination information storage unit 451 stores therein, for example, light emission patterns of the light sources corresponding to set quantities of light (in this case, quantities of illumination light emitted by the light source device 3).

Furthermore, the storage unit 45 stores therein various programs including an image acquisition processing program for the processing device 4 to execute an image acquisition processing method. The various programs may be widely distributed by being recorded in a computer readable recording medium, such as a hard disk, a flash memory, a CD-ROM, a DVD-ROM, or a flexible disk. These various programs may be obtained by being downloaded via a communication network. The communication network referred to herein is implemented by, for example, an existing public network, a local area network (LAN), or a wide area network (WAN), and may be wired or wireless.

The storage unit 45 configured as described above is implemented by use of, for example: a read only memory (ROM) having the various programs installed therein beforehand; and a RAM or a hard disk storing therein arithmetic operation parameters and data for processing.

The display device 5 displays a display image corresponding to an image signal received from the processing device 4 (the image processing unit 41) via a video cable. The display device 5 is configured by use of a liquid crystal or organic electroluminescence (EL) monitor, for example.

In the above described first embodiment, the diffuser 317 that diffuses part of light incident on the condenser lens 314 is provided in a part of the condenser lens 314, the part of light diffused by the diffuser 317 is input to the light quantity sensor 315, and quantity of light is detected by the light quantity sensor 315. According to this first embodiment, just providing the diffuser 317 in a part of the condenser lens 314 enables part of light to be input to the light quantity sensor 315 provided outside the optical path, and as a result, upsizing is prevented and quantity of illumination light is able to be detected.

First Modified Example of First Embodiment

Figure 6:
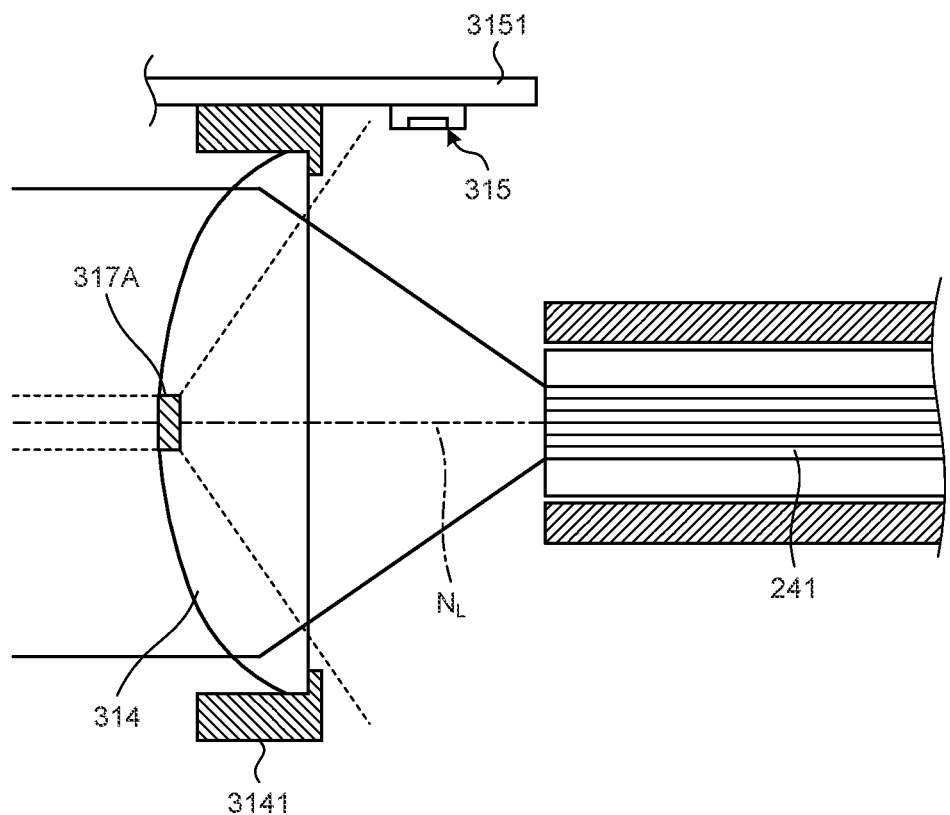
FIG. 6 is a diagram illustrating a configuration of a portion of a light source device in an endoscope system according to a first modified example of the first embodiment of the disclosure, the portion being where a light guide is connected.

A first modified example of the first embodiment of the disclosure will be described next by reference to FIG. 6. FIG. 6 is a diagram illustrating a configuration of a portion of a light source device in an endoscope system according to the first modified example of the first embodiment of the disclosure, the portion being where a light guide is connected. The endoscope system according to the first modified example has the same configuration as the endoscope system 1 described above, except that the position where the diffuser 317 is installed has been changed in the first modified example. A diffuser 317A configured differently from that of the first embodiment will thus be described hereinafter.

Similarly to the diffuser 317, the diffuser 317A is provided between a condenser lens 314 and a multiplexer and diffuses light incident thereon. The diffuser 317A is formed by surface processing of the condenser lens 314. The diffuser 317A is provided: on a side of the condenser lens 314, the side being opposite to a side facing a light guide 241; and at the center of the condenser lens 314, the center being where an optical axis $N_L$ of an illumination optical system including the condenser lens 314 passes. In this first modified example also, part of light diffused by the diffuser 317A is input to a light quantity sensor 315 via the condenser lens 314.

Similarly to the first embodiment, in the first modified example, the diffuser 317A that diffuses part of light incident on the condenser lens 314 is provided in a part of the condenser lens 314, the part of light diffused by the diffuser 317A is input to the light quantity sensor 315, and quantity of light is detected by the light quantity sensor 315. According to this first modified example, just providing the diffuser 317A in a part of the condenser lens 314 enables part of light to be input to the light quantity sensor 315 provided outside the optical path, and as a result, upsizing is prevented and quantity of illumination light is able to be detected.

Furthermore, because the diffuser 317A is arranged at the center of the condenser lens 314 in this first modified example, positioning is not needed when the condenser lens 314 is attached to a lens holder 3141 and the condenser lens 314 is thus able to be attached to the lens holder 3141 easily. In contrast, because the diffuser 317 of the first embodiment is arranged at a position deviated from the center of the condenser lens 314, positioning of the diffuser 317 about the central axis of the condenser lens 314 is needed when the condenser lens 314 is attached to the lens holder 3141.

Second Modified Example of First Embodiment

Figure 7:
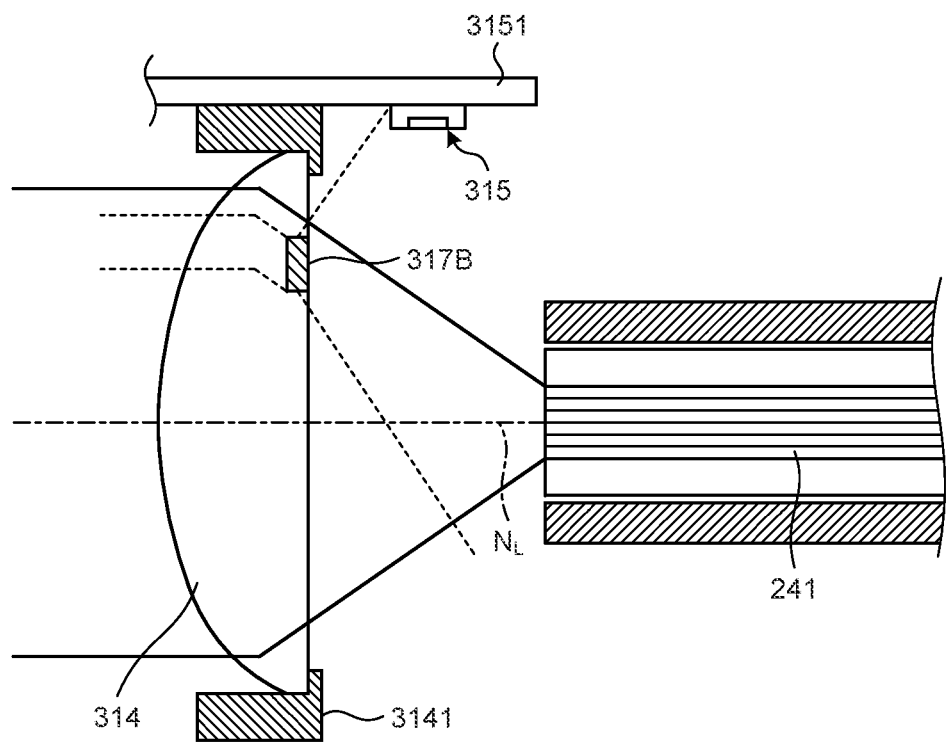
FIG. 7 is a diagram illustrating a configuration of a portion of a light source device in an endoscope system according to a second modified example of the first embodiment of the disclosure, the portion being where a light guide is connected.

A second modified example of the first embodiment of the disclosure will be described next by reference to FIG. 7. FIG. 7 is a diagram illustrating a configuration of a portion of a light source device in an endoscope system according to the second modified example of the first embodiment of the disclosure, the portion being where a light guide is connected. The endoscope system according to the second modified example has the same configuration as the endoscope system 1 described above, except that the position where the diffuser 317 is installed has been changed in the second modified example. A diffuser 317B configured differently from that of the first embodiment will thus be described hereinafter.

Similarly to the diffuser 317, the diffuser 317B is provided between a condenser lens 314 and a multiplexer and diffuses light incident thereon. The diffuser 317B is formed by surface processing of the condenser lens 314. The diffuser 317B is provided: on a side of the condenser lens 314, the side facing a light guide 241; and at a position deviated from an optical axis $N_L$ of an illumination optical system including the condenser lens 314. The diffuser 317B may be provided at the center of the condenser lens 314, the center being where the optical axis $N_L$ of the illumination optical system including the condenser lens 314 passes, similarly to the first modified example. In this second modified example also, part of light diffused by the diffuser 317B is input to a light quantity sensor 315.

Similarly to the first embodiment, in the second modified example, the diffuser 317B that diffuses part of light incident on the condenser lens 314 is provided in a part of the condenser lens 314, the part of light diffused by the diffuser 317B is input to the light quantity sensor 315, and quantity of light is detected by the light quantity sensor 315. According to this second modified example, just providing the diffuser 317B in a part of the condenser lens 314 enables part of light to be input to the light quantity sensor 315 provided outside the optical path, and as a result, upsizing is prevented and quantity of illumination light is able to be detected.

Furthermore, according to the second modified example, because light is diffused at a position closer to the light quantity sensor 315 than in the configuration using the diffuser 317 or 317A, light is able to be guided to the light quantity sensor 315 even more efficiently than in the first embodiment.

Second Embodiment

Figure 8:
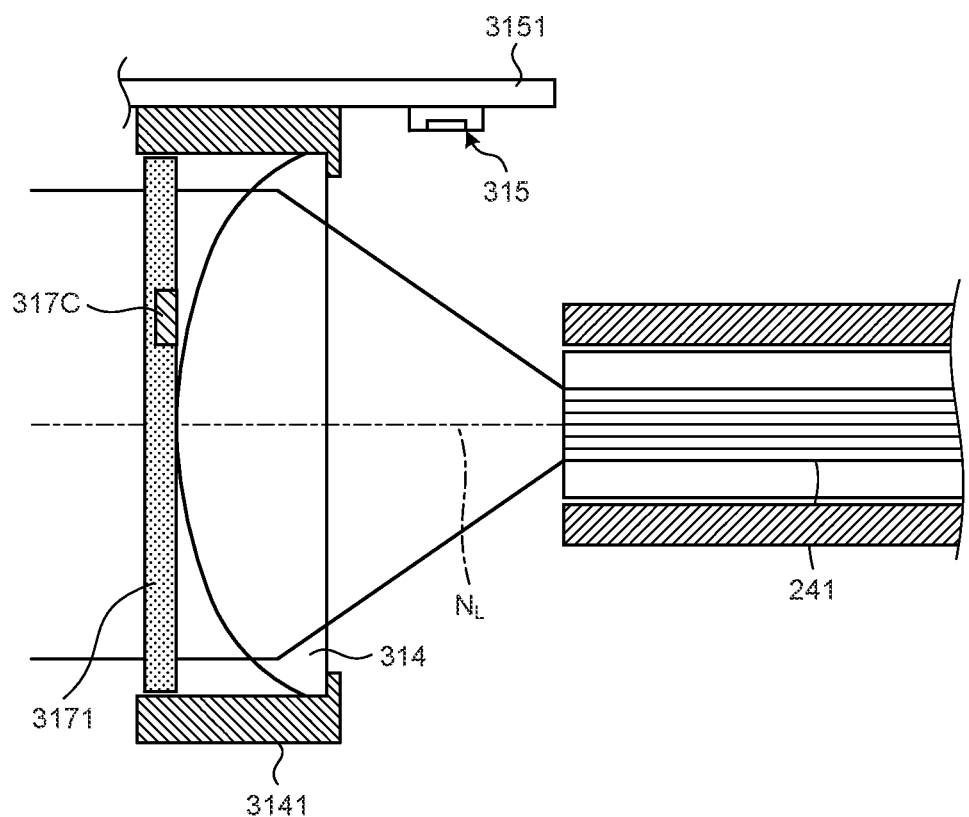
FIG. 8 is a diagram illustrating a configuration of a portion of a light source device in an endoscope system according to a second embodiment of the disclosure, the portion being where a light guide is connected.

A second embodiment of the disclosure will be described next by reference to FIG. 8. FIG. 8 is a diagram illustrating a configuration of a portion of a light source device in an endoscope system according to the second embodiment of the disclosure, the portion being where a light guide is connected. The endoscope system according to the second embodiment has the same configuration as the endoscope system 1 described above, except that the position where the diffuser 317 is installed has been changed in this second embodiment. A diffuser 317C configured differently from that of the first embodiment will thus be described hereinafter.

The diffuser 317C is formed in a holder 3171 provided adjacent to the condenser lens 314 along an optical axis $N_L$ direction. The holder 3171 is configured by use of a material high in transmittance of light, for example, glass. The holder 3171 corresponds to a transmissive material.

The diffuser 317C is formed by surface processing of the holder 3171. The diffuser 317C is formed on one surface or both surfaces of the holder 3171. The holder 3171 is provided on an opposite side of the condenser lens 314, the opposite side being opposite to a side facing the light guide 241. Because the holder 3171 is provided between the condenser lens 314 and a multiplexer, the diffuser 317C is positioned between the condenser lens 314 and the multiplexer. Furthermore, the diffuser 317C is provided at a position deviated from an optical axis $N_L$ of an illumination optical system including the condenser lens 314 when the holder 3171 is installed in a light source device 3. The diffuser 317B may be provided at the center of the condenser lens 314, the center being where the optical axis $N_L$ of the illumination optical system including the condenser lens 314 passes, similarly to the first modified example. In this second embodiment also, part of light diffused by the diffuser 317C is input to a light quantity sensor 315 via the condenser lens 314.

In this second embodiment, the diffuser 317C that diffuses part of light incident on the condenser lens 314 is provided in the holder 3171 provided adjacent to the condenser lens 314, the part of light diffused by the diffuser 317C is input to the light quantity sensor 315, and quantity of light is detected by the light quantity sensor 315. According to this second embodiment, just providing the diffuser 31C7 in a part of the holder 3171 enables part of light to be input to the light quantity sensor 315 provided outside the optical path, and as a result, upsizing is prevented and quantity of illumination light is able to be detected.

Furthermore, in this second embodiment, because the diffuser 317C is formed in a member (the holder 3171) different from the condenser lens 314, installation of the diffuser 317C in the optical path is easier than that in a case where the condenser lens 314 is directly processed.

Third Embodiment

Figure 9:
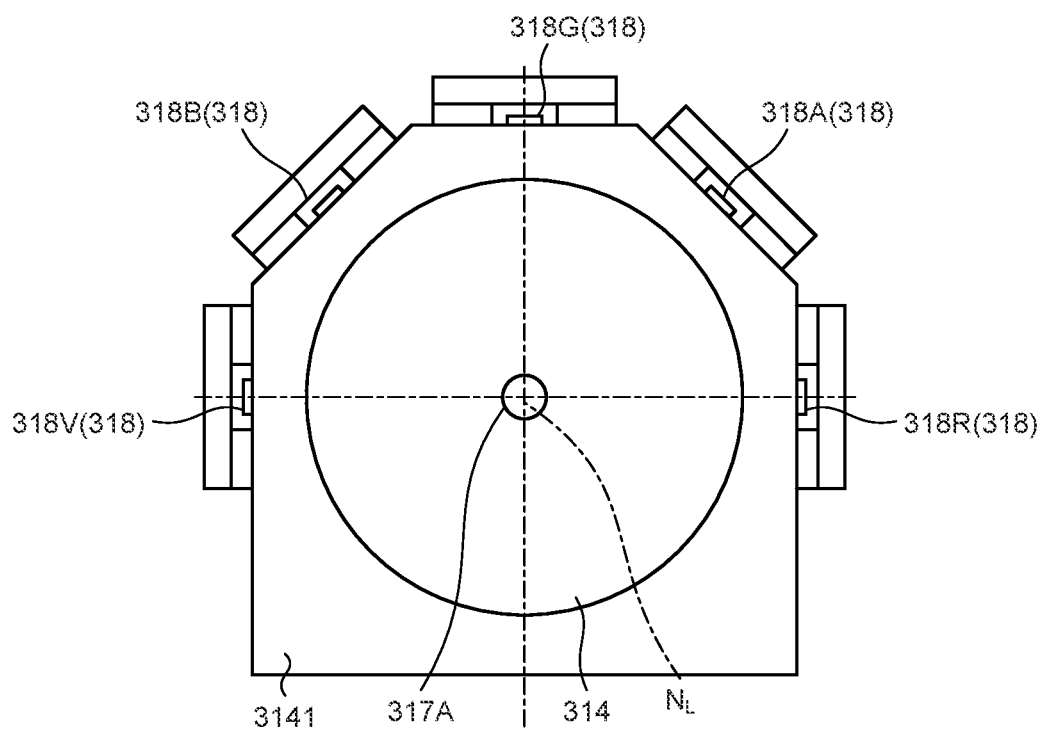
FIG. 9 is a plan view of a region around a condenser lens in a light source device of an endoscope system according to a third embodiment of the disclosure.

A third embodiment of the disclosure will be described next by reference to FIG. 9. FIG. 9 is a diagram illustrating a configuration of a portion of a light source device in an endoscope system according to the third embodiment of the disclosure, the portion being where a light guide is connected. The endoscope system according to the third embodiment has a configuration that is the same as that of the endoscope system 1 described above, except that the diffuser 317 has been replaced by the diffuser 317A of the first modified example and the configuration of the light quantity sensor 315 has been changed in the third embodiment. A light quantity sensor 318 having a configuration different from those of the first embodiment and the first modified example will thus be described hereinafter.

The light quantity sensor 318 includes a first sensor 318V, a second sensor 318B, a third sensor 318G, a fourth sensor 318A, and a fifth sensor 318R. The light quantity sensor 318 is held by a lens holder 3141.

The first sensor 318V has sensitivity to light of a wavelength band emitted by a first light source 311V.

The second sensor 318B has sensitivity to light of a wavelength band emitted by a second light source 311B.

The third sensor 318G has sensitivity to light of a wavelength band emitted by a third light source 311G.

The fourth sensor 318A has sensitivity to light of a wavelength band emitted by a fourth light source 311A.

The fifth sensor 318R has sensitivity to light of a wavelength band emitted by a fifth light source 311R.

The first sensor 318V to the fifth sensor 318R are provided at positions on one side of a condenser lens 314, the one side being near a light guide 241 (a downstream side along an optical path) and peripheral to the condenser lens 314 as viewed along an optical axis $N_L$ direction. Distances between these sensors and the diffuser 317A may be the same or may be set according to representative values for the wavelength bands emitted by the light sources.

Furthermore, the first sensor 318V to the fifth sensor 318R have light receiving surfaces that are orthogonal to radial directions of the condenser lens 314. That is, the light receiving surfaces of the first sensor 318V to fifth sensor 318R all face the center of the condenser lens 314.

In the third embodiment, the diffuser 317A that diffuses part of light incident on the condenser lens 314 is provided in a part of the condenser lens 314, the part of light diffused by the diffuser 317A is input to the light quantity sensor 318, and quantity of light is detected by the light quantity sensor 318. According to this third embodiment, just providing the diffuser 317A in a part of the condenser lens 314 enables part of light to be input to the light quantity sensor 318 provided outside the optical path, and as a result, upsizing is prevented and quantity of illumination light is able to be detected.

Furthermore, in this third embodiment, because light diffused by the diffuser 317A is detected individually for respective wavelength bands by the first sensor 318V to fifth sensor 318R, just providing filters that transmit light of wavelength bands to be detected for the same monochrome photodiodes enables these sensors to be formed and enables comparatively inexpensive manufacture.

Fourth Embodiment

Figure 10:
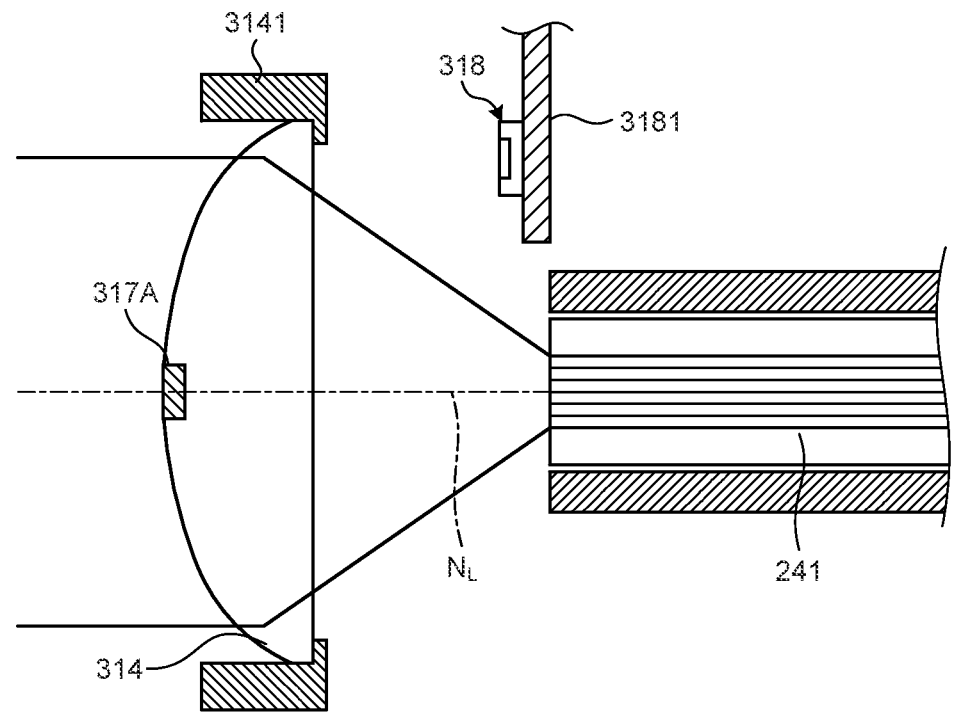
FIG. 10 is a diagram illustrating a configuration of a portion of a light source device in an endoscope system according to a fourth embodiment of the disclosure, the portion being where a light guide is connected.
Figure 11:
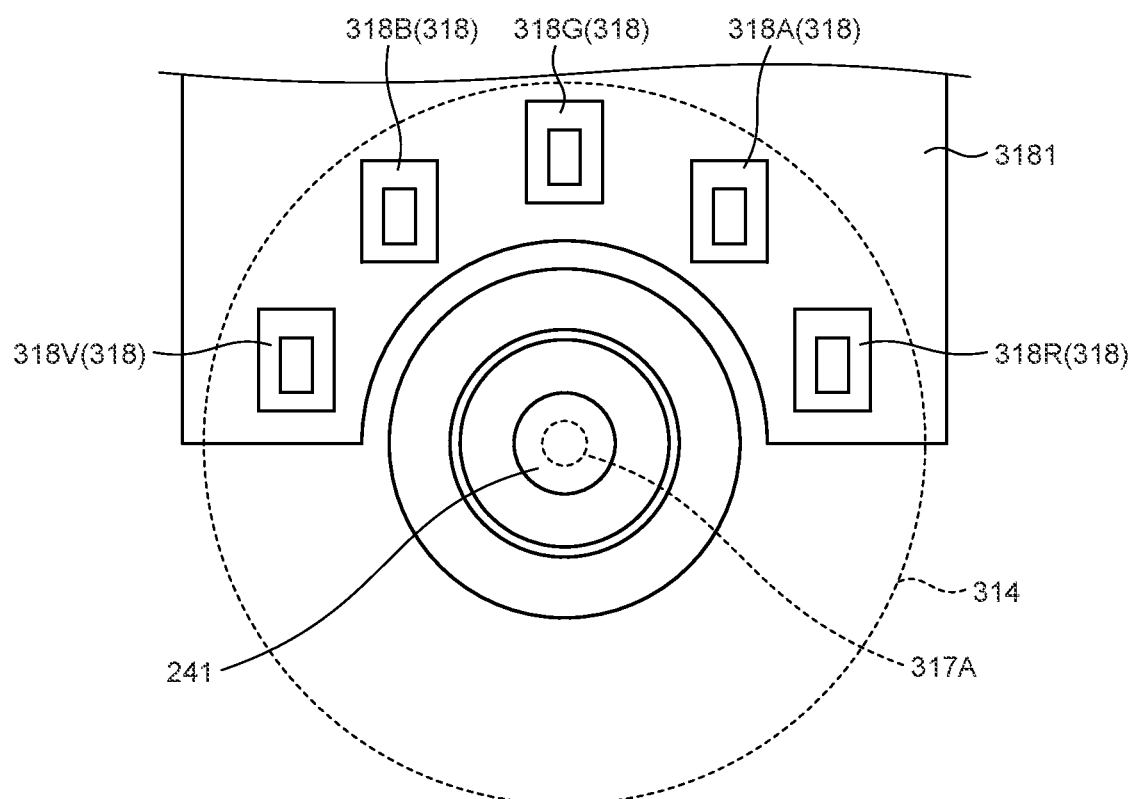
FIG. 11 is a plan view of a region around a condenser lens in the light source device of the endoscope system according to the fourth embodiment of the disclosure.

A fourth embodiment of the disclosure will be described next by reference to FIG. 10 and FIG. 11. FIG. 10 is a diagram illustrating a configuration of a portion of a light source device in an endoscope system according to the fourth embodiment of the disclosure, the portion being where a light guide is connected. FIG. 11 is a plan view of a region around a condenser lens in the light source device of the endoscope system according to the fourth embodiment of the disclosure, as viewed along an optical axis direction. The endoscope system according to the fourth embodiment has a configuration that is the same as that of the third embodiment described above, except that the arrangement of the sensors of the light quantity sensor 318 has been changed in this fourth embodiment. Arrangement of a light quantity sensor 318 will thus be described hereinafter, the arrangement being different from that of the third embodiment.

A first sensor 318V to a fifth sensor 318R are held by a holder 3181 provided at a position on one side of a condenser lens 314, the one side being near a light guide 241 (a downstream side along an optical path). The sensors held by the holder 3181 are provided peripheral to the condenser lens 314 as viewed along an optical axis $N_L$ direction (see FIG. 11).

Furthermore, the first sensor 318V to the fifth sensor 318R have light receiving surfaces that are orthogonal to the optical axis $N_L$ direction. That is, the light receiving surfaces of the first sensor 318V to fifth sensor 318R all face a surface of the condenser lens 314.

In the fourth embodiment, a diffuser 317A that diffuses part of light incident on the condenser lens 314 is provided in a part of the condenser lens 314, the part of light diffused by the diffuser 317A is input to the light quantity sensor 318, and quantity of light is detected by the light quantity sensor 318. According to this fourth embodiment, just providing the diffuser 317A in a part of the condenser lens 314 enables part of light to be input to the light quantity sensor 318 provided outside the optical path, and as a result, upsizing is prevented and quantity of illumination light is able to be detected.

Furthermore, similarly to the third embodiment, in this fourth embodiment, because light diffused by the diffuser 317A is individually detected for respective wavelength bands by the first sensor 318V to fifth sensor 318R, just providing filters that transmit light of wavelength bands to be detected for the same monochrome photodiodes enables the sensors to be formed and enables comparatively inexpensive manufacture.

Fifth Embodiment

Figure 12:
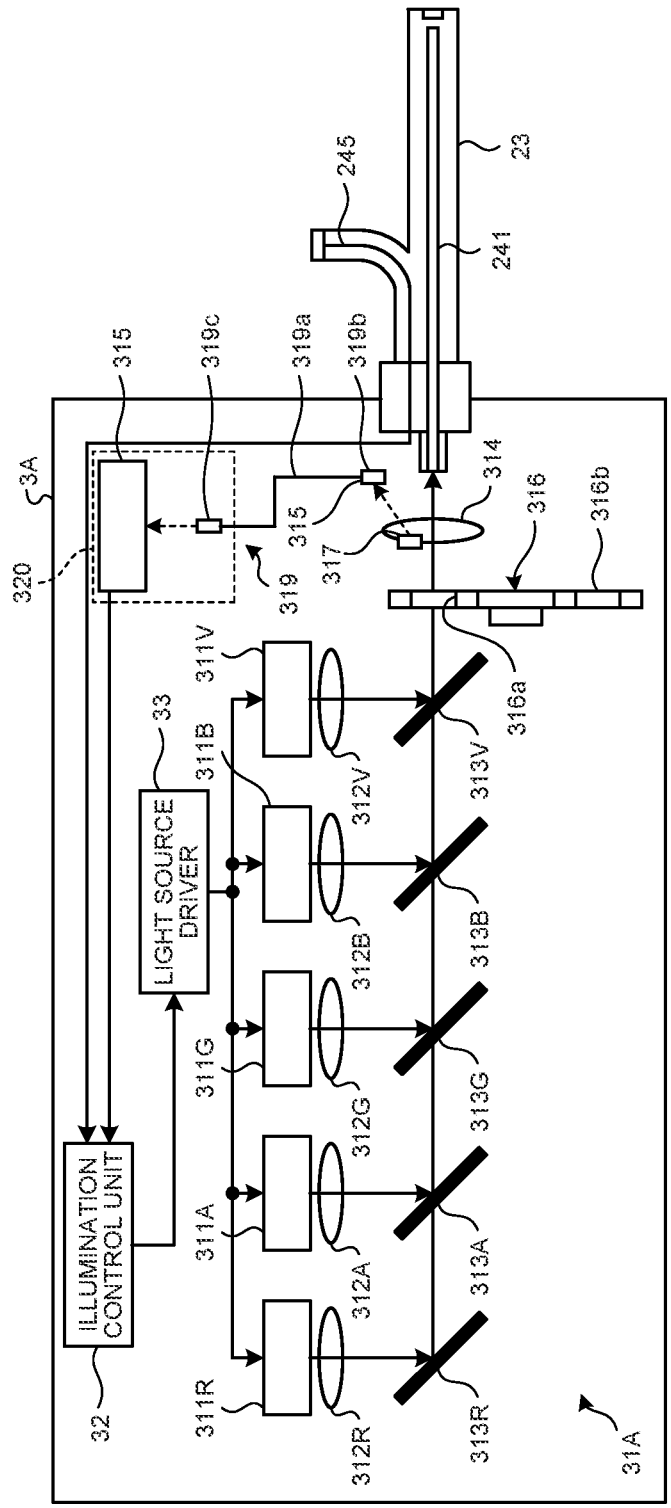
FIG. 12 is a diagram illustrating a configuration of a light source device in an endoscope system according to a fifth embodiment of the disclosure.
Figure 13:
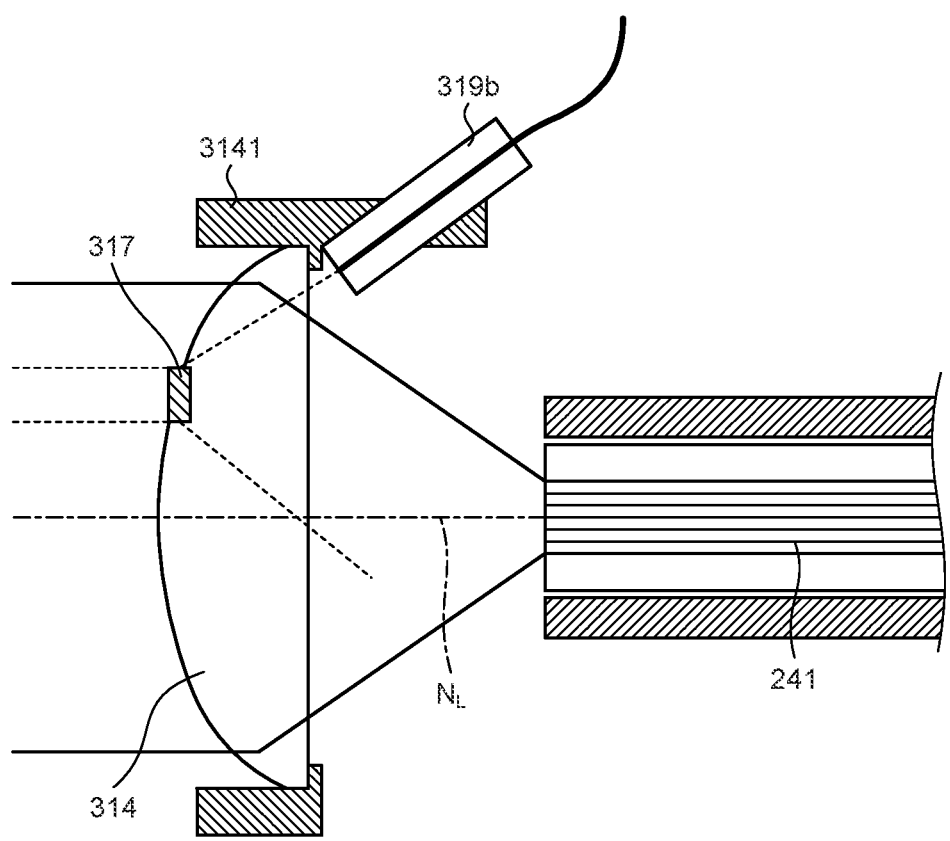
FIG. 13 is a diagram illustrating a configuration of a portion of the light source device in the endoscope system according to the fifth embodiment of the disclosure, the portion being where a light guide is connected.

A fifth embodiment of the disclosure will be described next by reference to FIG. 12 and FIG. 13. FIG. 12 is a diagram illustrating a configuration of a light source device in an endoscope system according to the fifth embodiment of the disclosure. FIG. 13 is a diagram illustrating a configuration of a portion of the light source device in the endoscope system according to the fifth embodiment of the disclosure, the portion being where a light guide is connected. The endoscope system according to the fifth embodiment is the same as the endoscope system 1 except that the light guiding means for light diffused by the diffuser 317 has been changed in the fifth embodiment. A configuration of a light source device 3A will thus be described hereinafter, the configuration being different from that of the first embodiment.

A light source unit 31A according to the fifth embodiment has an optical fiber 319 provided between a condenser lens 314 and a light quantity sensor 315. The optical fiber 319 includes a fiber portion 319a that guides light, an input end 319b that is provided at one end of the fiber portion 319a and is where light diffused by a diffuser 317 is input to, and an output end 319c that is provided at the other end of the fiber portion 319a and is where the light guided by the fiber portion 319a is output from. The input end 319b is provided: on one side of the condenser lens 314, the one side being near a light guide 241; and at a position deviated from an optical axis $N_L$ of an illumination optical system including the condenser lens 314. The output end 319c is provided to face a light receiving surface of the light quantity sensor 315. Part of light diffused by the diffuser 317 enters the optical fiber 319 after passing through the condenser lens 314. The light output from the output end 319c via the fiber portion 319a is input to sensors (a first sensor 315A and a second sensor 315B) of the light quantity sensor 315. The first sensor 315A and the second sensor 315B are arranged to face a light output surface of the output end 319c. A spectroscopic means, such as a prism, may be provided at the output end 319c to cause light separated by the spectroscopic means to be input to the first sensor 315A and the second sensor 315B.

Furthermore, the output end 319c and the light quantity sensor 315 are provided in a light-shielding space 320 formed of a light-shielding member and are thus configured to be shielded from external light. The input end 319b is held by a lens holder 3141.

In the fifth embodiment, similarly to the first embodiment, the diffuser 317 that diffuses part of light incident on the condenser lens 314 is provided in a part of the condenser lens 314, the part of light diffused by the diffuser 317 is input to the light quantity sensor 315 via the optical fiber 319, and quantity of light is detected by the light quantity sensor 315. According to this fifth embodiment, just providing the diffuser 317 in a part of the condenser lens 314 in an optical path of illumination light enables part of light to be input to the light quantity sensor 315 provided outside the optical path, and as a result, upsizing is prevented and quantity of illumination light is able to be detected.

Furthermore, because this fifth embodiment is provided with the optical fiber 319 between the condenser lens 314 and the light quantity sensor 315 and is thus configured to guide part of diffused light, light transmitted between the condenser lens 314 and the light quantity sensor 315 is able to be input to the light quantity sensor 315 even more infallibly.

Sixth Embodiment

A sixth embodiment of the disclosure will be described next by reference to FIG. 14. FIG. 14 is a diagram illustrating a configuration of a light source device in an endoscope system according to the sixth embodiment of the disclosure. The endoscope system according to the sixth embodiment is the same as the endoscope system 1 except that the mode of installation of the diffuser 317 has been changed in the sixth embodiment. A light source unit 31B of a light source device 3B will thus be described hereinafter, the light source unit 31B having a configuration different from that of the first embodiment.

The light source unit 31B includes a first light source 311V to a fifth light source 311R, a lens 312V to a lens 312R, a first dichroic mirror 313V to a fifth dichroic mirror 313R, a condenser lens 314, a light quantity sensor 315, a rotating filter 316A, and a diffuser 317D.

The rotating filter 316A includes a hole 316a where illumination light that has been multiplexed is passed through and a transmissive portion 316c provided with the diffuser 317D that diffuses part of the illumination light. The transmissive portion 316c is configured by use of a material high in transmittance of light, for example, glass. The rotating filter 316A is provided between the first dichroic mirror 313V and the condenser lens 314, and inserts or removes the hole 316a or the transmissive portion 316c into and from an optical path for illumination light by rotating itself under control of the illumination control unit 32. Because the rotating filter 316A is provided between the condenser lens 314 and a multiplexer, the diffuser 317D is positioned between the condenser lens 314 and the multiplexer. The rotating filter 316A may further include a wavelength selecting filter 316b described above. In a case where the rotating filter 316A includes the wavelength selecting filter 316b, a diffuser may be provided in the wavelength selecting filter 316b for detection of quantity of excitation light, for example. In this case, the diffuser may be provided in a transmissive material provided over the wavelength selecting filter 316b or may be provided by processing of a part of the wavelength selecting filter 316b.

The diffuser 317D is provided at a position deviated from an optical axis $N_L$ of an illumination optical system including the condenser lens 314 when the transmissive portion 316c has been arranged in the optical path. The diffuser 317D may be provided at the center of the condenser lens 314, the center being where the optical axis $N_L$ of the illumination optical system including the condenser lens 314 passes, similarly to the first modified example. In this sixth embodiment also, part of light diffused by the diffuser 317D is input to the light quantity sensor 315 via the condenser lens 314.

In the sixth embodiment, the diffuser 317D is provided in the rotating filter 316A, part of light diffused by the diffuser 317D is input to the light quantity sensor 315, and quantity of light is detected by the light quantity sensor 315. According to this sixth embodiment, just providing the diffuser 317D in the rotating filter 316A in the optical path of illumination light enables part of light to be input to the light quantity sensor 315 provided outside the optical path, and as a result, upsizing is prevented and quantity of illumination light is able to be detected.

Furthermore, in this sixth embodiment, because the diffuser 317D is able to be inserted into or removed from the optical path by the rotating filter 316A, the diffuser 317D is able to be removed from the optical path when detection of quantity of light is not needed. Removing the diffuser 317D from the optical path enables illumination light to be input to the light guide 241, the illumination light having passed the first dichroic mirror 313V, without any leakage caused by diffusion.

With respect to the sixth embodiment, the example where part of light diffused by the diffuser 317D is input to the light quantity sensor 315 via the condenser lens 314 has been described, but the part of light may be input directly to the light quantity sensor 315 from the diffuser 317D without going through the condenser lens 314. In this case, the diffuser 317D is provided between the rotating filter 316A and the condenser lens 314, for example.

With respect to each of the first to sixth embodiments, the example where the light source device 3 is separately bodied from the processing device 4 has been described above, but a configuration with the light source device 3 and the processing device 4 integrated with each other may be adopted instead.

Furthermore, with respect to each of the first to sixth embodiments, the example where quantities of light of target wavelength bands are detected by plural sensors has been described above, but a configuration provided with a single light quantity sensor that receives white light and detects quantity of white light may be adopted instead.

Furthermore, each of the first to fourth and sixth embodiments described above may be configured by being provided with a spectroscopic means, such as a prism, between the condenser lens 314 and the light quantity sensor 315, to separate light of wavelength bands to be detected and detect the separated light by means of plural sensors. This spectroscopic configuration enables detection of quantities of light of respective wavelength bands by arrangement of monochrome photodiodes at positions where light of the wavelength bands are dispersed to. The photodiodes arranged at the respective dispersed positions may be of the same type.

Furthermore, according to the above description of the first to sixth embodiments, the endoscope system according to the disclosure is the endoscope system 1 where the endoscope 2 is used, the endoscope 2 being flexible and being for observation of body tissue inside subjects, but the endoscope system is also applicable to an endoscope system where any of different types of endoscopes is/are used, the different types of endoscopes including a rigid endoscope, an industrial endoscope for observation of characteristics of materials, a fiberscope, and a device having a camera head connected to an eyepiece unit of an optical endoscope, such as an optical telescope.

The disclosure has an effect of enabling detection of quantity of illumination light while preventing upsizing.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A light source device for use with a medical device, the light source device comprising:
   a first light source configured to emit light of a first wavelength;
   a second light source configured to emit light of a second wavelength;
   a multiplexer configured to multiplex the light emitted by the first and second light sources and direct multiplexed light to an optical path;
   a diffuser provided between the multiplexer and an input end of a light guide disposed in the optical path, the diffuser configured to diffuse a portion of the multiplexed light to an outside of the optical path;
   a sensor provided outside the optical path and the sensor is positioned between the diffuser and the input end of the light guide, the sensor configured to detect a quantity of at least the portion of the light diffused by the diffuser; and
   a condenser lens on which the multiplexed light is incident, the condenser lens configured to condense the incident multiplexed light to the input end of the light guide,
   wherein the diffuser is provided in a portion of the condenser lens.

2. The light source device according to claim 1, wherein the sensor is configured to detect a quantity of the light of each of the first wavelength and the second wavelength, from the light diffused by the diffuser.

3. The light source device according to claim 1, wherein the diffuser is arranged peripheral to a center of the condenser lens, the center being on an optical axis of the optical path.

4. The light source device according to claim 1, wherein the diffuser is arranged at a position including a center of the condenser lens, the center being on an optical axis of the optical path.

5. The light source device according to claim 1, further comprising:
   a holder provided on one side of the condenser lens, the one side being a side of the condenser lens closer to the light guide, the holder being configured to hold the sensor.

6. The light source device according to claim 1, wherein the sensor including a first filter configured to transmit therethrough the light of the first wavelength and a second filter configured to transmit therethrough the light of the second wavelength.

7. The light source device according to claim 1, wherein the sensor comprises:
   a first sensor configured to detect a quantity of the light of the first wavelength; and
   a second sensor configured to detect quantity of the light of the second wavelength.

8. The light source device according to claim 1, further comprising:
   a controller configured to control, based on a detection result of the sensor, a quantity of light emitted by at least one of the first and second light sources.

9. The light source device according to claim 1, wherein the second wavelength is different from the first wavelength.

10. The light source device according to claim 1, wherein the first wavelength is a first wavelength band and the second wavelength is a second wavelength band.

11. The light source device according to claim 1, further comprising a third light source configured to emit light of a third wavelength;
   wherein the multiplexer is configured to multiplex the light emitted by the first, second and third light sources and direct the multiplexed light to the optical path.

12. The light source device according to claim 11, further comprising a fourth light source configured to emit light of a fourth wavelength;
   wherein the multiplexer is configured to multiplex the light emitted by the first, second, third and fourth light sources and direct the multiplexed light to the optical path.

13. The light source device according to claim 12, further comprising a fifth light source configured to emit light of a fifth wavelength;
   wherein the multiplexer is configured to multiplex the light emitted by the first, second, third, fourth and fifth light sources and direct the multiplexed light to the optical path.

14. The light source device according to claim 1, wherein the sensor comprising first and second sensors, for detecting the first and second wavelengths, respectively, from at least the portion of the light diffused by the diffuser; and
   the first and second sensors are positioned separated in a direction orthogonal to an optical axis direction.

15. A method for adjusting a light quantity provided to a medical device, the method comprising:
   emitting light of a first wavelength by a first light source;
   emitting light of a second wavelength by a second light source;
   combining, by a multiplexer, the light emitted by the first and second light sources, and directing combined light to an optical path;
   diffusing, by a diffuser positioned between the multiplexer and an input end of the light guide, a portion of the combined light to an outside of the optical path;
   condensing, by a condenser lens on which the multiplexed light is incident, the condenser lens configured to condense the incident multiplexed light to the input end of the light guide, wherein the diffuser is provided in a portion of the condenser lens;
   providing a sensor outside the optical path for the input to the light guide;
   detecting, by a sensor positioned outside the optical path of the light guide and the sensor is positioned between the diffuser and the input end of the light guide, a quantity of at least the portion of the light diffused by the diffuser; and
   controlling a quantity of light emitted by at least one of the first and second light sources based on a detection result of the sensor.

* * * * *